United States Patent [19]

Isakson et al.

[11] Patent Number: 5,700,816
[45] Date of Patent: Dec. 23, 1997

[54] TREATMENT OF INFLAMMATION AND INFLAMMATION-RELATED DISORDERS WITH A COMBINATION OF A CYCLOOXYGENASE-2 INHIBITOR AND A LEUKOTRIENE $A_4$ HYDROLASE INHIBITOR

[76] Inventors: Peter C. Isakson, 2292 Ridgley Woods Dr., Clarkson Valley, Mo. 63005; Gary D. Anderson, 1886 Woodhollow Dr. #203, Maryland Heights, Mo. 63043; Susan A. Gregory, 4400 Lindell Blvd., #20A, St. Louis, Mo. 63108

[21] Appl. No.: 489,468

[22] Filed: Jun. 12, 1995

[51] Int. Cl.$^6$ .................. A61K 31/445; A61K 31/40; A61K 31/38; A61K 31/20; A61K 31/18; A61K 31/415; A61K 31/195; A61K 31/135

[52] U.S. Cl. .................. 514/326; 514/330; 514/317; 514/422; 514/445; 514/438; 514/559; 514/602; 514/603; 514/406; 514/407; 514/403; 514/404; 514/567; 514/381; 514/648

[58] Field of Search .................. 514/406, 407, 514/403, 404, 567, 381, 648, 326, 330, 317, 422, 445, 438, 559, 602, 603

[56] References Cited

U.S. PATENT DOCUMENTS

| | | | |
|---|---|---|---|
| 5,344,991 | 9/1994 | Reitz et al. | 568/34 |
| 5,380,738 | 1/1995 | Norman et al. | 514/374 |
| 5,393,790 | 2/1995 | Reitz et al. | 514/709 |
| 5,466,823 | 11/1995 | Talley et al. | 548/377.1 |

FOREIGN PATENT DOCUMENTS

| | | |
|---|---|---|
| 360246 | 9/1989 | European Pat. Off. . |
| 94/00420 | 1/1994 | WIPO . |
| 94/13635 | 6/1994 | WIPO . |
| 94/15932 | 7/1994 | WIPO . |
| 94/20480 | 9/1994 | WIPO . |
| 94/26731 | 11/1994 | WIPO . |
| 94/27980 | 12/1994 | WIPO . |
| 95/00501 | 1/1995 | WIPO . |

OTHER PUBLICATIONS

J. Allergy Clinl Immunol., 81, 110 (1988).
J. Basamajian, Spine, 14, 438 (1989).
V. Fossaluzza et al, Int. J. Clin. Pharm. Res., XII, 99 (1992).
R. Greenwald et al, J. Rheumatol., 19, 927 (1992).
W. Beaver, Am. J. Med., 77, 38 (1984).
L. Guth et al., Proc. Natl. Acad. Sci. USA, 91, 12308 (1994).
G. Hughes et al, Dermatology, 184, 54 (1992).
C. Stewart et al, Clin. Pharmacol. Ther., 47, 540 (1990).
K. Tramposch, Inflammation, 17, 531 (1993).
S. Lightman et al, Am. J. Ophthalmol., 108, 95 (1989).
B. Teicher et al., Cancer Chemother. Pharmacol., 33, 515 (1994).
R. Willikens et al, Arthritis Rheum., 19, 677 (1976).
P. Seideman et al, ACTA Orthop. Scand., 64, 285 (1993).
M. Seifert et al, Curr. Med. Res. Opin., 7, 38 (1980).

*Primary Examiner*—William R. A. Jarvis
*Attorney, Agent, or Firm*—Joseph W. Bulock

[57] ABSTRACT

Combinations of a cyclooxygenase-2 inhibitor and a leukotriene $A_4$ hydrolase inhibitor are described for treatment of inflammation and inflammation-related disorders.

21 Claims, No Drawings

TREATMENT OF INFLAMMATION AND INFLAMMATION-RELATED DISORDERS WITH A COMBINATION OF A CYCLOOXYGENASE-2 INHIBITOR AND A LEUKOTRIENE A₄ HYDROLASE INHIBITOR

FIELD OF THE INVENTION

This invention is in the field of antiinflammatory pharmaceutical agents and specifically relates to co-administration of an inhibitor of cyclooxygenase-2 and a leukotriene A₄ hydrolase inhibitor for treating inflammation and inflammation-related disorders, such as arthritis.

BACKGROUND OF THE INVENTION

Prostaglandins play a major role in the inflammation process, and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDS have been found to prevent the production of prostaglandins by inhibiting enzymes in the human arachidonic acid/prostaglandin pathway including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

In another portion of the arachidonic acid pathway, physiologically active leukotrienes, such as leukotriene $B_4$ ($LTB_4$), leukotriene $C_4$ ($LTC_4$) and leukotriene $D_4$ ($LTD_4$) and other metabolites, are produced by the 5-lipoxygenase-mediated (5-LO) oxidation of arachidonic acid. These leukotrienes have been implicated in various inflammation-related disorders and allergic diseases, and thus compounds which inhibit leukotriene $A_4$ conversion to leukotriene $B_4$, such as compounds which inhibit leukotriene $A_4$ hydrolase are useful in the treatment of disease states in which leukotrienes play an important role.

It is believed that selective inhibitors of cyclooxygenase-2 and of leukotriene $A_4$ hydrolase, which affect the two enzymes at low concentrations, will decrease the incidence and severity more completely. These compositions also will beneficially affect the damage caused by the various inflammatory diseases and inflammation-related disorders mediated by cyclooxygenase-2 and leukotriene $A_4$ hydrolase. These compositions also will not have the level of gastrointestinal side effects commonly associated with traditional NSAIDs.

Compounds which selectively inhibit cyclooxygenase-2 have been described in U.S. Pat. Nos. 5,380,738, 5,344,991, 5,393,790 and WO documents WO94/15932, WO94/27980, WO95/00501, W094/13635, WO94/20480, and WO94/26731.

Compounds which inhibit leukotriene $A_4$ hydrolase have been described in co-pending U.S. patent application Ser. No. 08/321,184.

Combined therapies of NSAIDs and other reagents are known in the art. Brooks and Karl describe the treatment of hay fever with combined antihistamines and a cyclooxygenase-inhibiting drug (flurbiprofen) (J. Allergy Clin. Immunol., 81, 110 (1988)). J. Basmajian (Spine, 14, 438 (1989)) describes the combination of the analgesic diflunisal and an antispasm agent in the treatment of back pain. V. Fossaluzza and S DeVita describe the combined therapy of ibuprofen and an antispasm agent to reduce morning stiffness associated with primary fibromyaglia syndrome (Int. J. Clin. Pharm. Res., XII, 99 (1992)). R. Greenwald et al. (J. Rheumatol., 19, 927 (1992)) report the combination of tetracycline and the NSAID flurbiprofen ameliorates the tissue damage associated with rheumatoid arthritis.

Combination analgesics have been reported (W. Beaver, Am. J. Med., 77, 38 (1984)) although such combinations do not substantially reduce adverse effects.

The combination of NSAIDs and steroids have been described. A combination of indomethacin, steroid and lipopolysaccharide has been reported for the treatment of spinal injury (L. Guth et al., Proc. Natl. Acad. Sci. USA, 91, 12308 (1994)). G. Hughes et al. describe combinations of corticosteroids with NSAIDs for the treatment of sunburn (Dermatology, 184, 54 (1992)). C. Stewart et al. (Clin. Pharmacol. Ther., 47, 540 (1990)) describe the combination of naproxen and methotrexate as safe, although concurrent administrations of methotrexate with other NSAIDs have been reported to be toxic and sometimes fatal. A combination of a dual 5-lipoxygenase/cyclooxygenase inhibitor with a glucocorticoid is described for the treatment of skin disorders (K. Tramposch, Inflammation, 17, 531 (1993)). Combinations of NSAIDs and steroids should be used in the treatment of scleritis only if patients are not responsive to any other treatment (S. Lightman and P. Watson, Am. J. Ophthalmol., 108, 95 (1989)).

Combinations of cyclooxygenase inhibitors, lipoxygenase inhibitors, collagenase inhibitors and cytotoxic agents have been used in the treatment of non-small-cell lung cancers (B. Teicher et al., Cancer. Chemother. Pharmacol., 33, 515 (1994)).

Combinations of naproxen with other NSAIDs have been described in the treatment of arthritis. R. Willikens and E. Segre (Arthritis Rheum., 19, 677 (1976)) describe the combination of aspirin and naproxen as being more effective than aspirin alone for the treatment of rheumatoid arthritis. Naproxen and acetaminophen together were described for treating the pain associated with arthritis (P. Seideman et al., Acta Orthop. Scand., 64, 285 (1993)). However, combinations of naproxen with indomethacin or ibuprofen offer no advantage in the treatment of arthritis (M. Seifert and C. Engler, Curr. Med. Res. Opin., 7, 38 (1980)).

There have been no reported combinations of a cyclooxygenase-2 selective inhibitor and a leukotriene $A_4$ hydrolase inhibitor.

DESCRIPTION OF THE INVENTION

The invention involves a method of treating a subject having inflammation or an inflammation-related disorder with a combination comprising a therapeutically-effective amount of a cyclooxygenase-2 inhibitor and a leukotriene $A_4$ hydrolase inhibitor.

In addition, the invention describes a combination comprising a therapeutically-effective amount of a leukotriene $A_4$ hydrolase inhibitor and a cyclooxygenase-2 inhibitor selected from Dupont Dup 697, Taisho NS-398, meloxicam, flosulide and compounds of Formula I

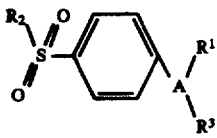

wherein A is a 5- or 6-member ring substituent selected from partially unsaturated or unsaturated heterocyclo and carbocyclic rings;
wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
wherein $R^2$ is selected from alkyl, and amino; and
wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

Combinations of the invention would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthma, bronchitis, menstrual cramps, tendinitis, bursitis, and skin related conditions such as psoriasis, eczema, burns and dermatitis. Combinations of the invention also would be useful to treat gastrointestinal conditions such as inflammatory bowel disease, Crohn's disease, gastritis, irritable bowel syndrome and ulcerative colitis and for the prevention of colorectal cancer. Combinations of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, conjunctivitis, swelling occurring after injury, myocardial ischemia, and the like. The combinations would also be useful for the treatment of certain central nervous system disorders such as alzheimers disease and dimentia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Besides being useful for human treatment, these compounds are also useful for treatment of mammals, including horses, dogs, cats, rats, mice, sheep, pigs, etc.

The term "cyclooxygenase-2 inhibitor" embraces compounds which selectively inhibit cyclooxygenase-2 over cyclooxygenase-1. Preferably, the compounds have a cyclooxygenase-2 $IC_{50}$ of less than about 0.5 µM, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 µM, and more preferably of greater than 20 µM. Such preferred selectivity may indicate an ability to reduce the incidence of common NSAID-induced side effects.

The term "leukotriene $A_4$ hydrolase inhibitor" embraces compounds which selectively inhibit leukotriene $A_4$ hydrolase with an $IC_{50}$ of less than about 10 µM. More preferably, the leukotriene $A_4$ hydrolase inhibitors have an $IC_{50}$ of less than about 1 µM.

The phrase "combination therapy" (or "co-therapy"), in defining use of a cyclooxygenase-2 inhibitor agent and a leukotriene $A_4$ hydrolase inhibitor agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent for use in the combination therapy which will achieve the goal of improvement in inflammation severity and the frequency of incidence over treatment of each agent by itself, while avoiding adverse side effects typically associated with alternative therapies.

A preferred class of compounds which inhibit cyclooxygenase-2 consists of compounds of Formula I wherein A is selected from oxazolyl, isoxazolyl, thienyl, dihydrofuryl, furyl, pyrrolyl, pyrazolyl, thiazolyl, imidazolyl, isothiazolyl, cyclopentenyl, phenyl, and pyridyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^3$ is a radical selected from halo, lower alkyl, oxo, cyano, carboxyl, lower cyanoalkyl, heteroaryloxy, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, heteroaryloxy, alkoxycarbonyl, aminocarbonyl, alkylaminocarbonyl, alkylamino, aminoalkyl, alkylaminoalkyl, aryloxy, and aralkoxy; or a pharmaceutically-acceptable salt thereof.

A more preferred class of compounds which inhibit cyclooxygenase-2 consists of compounds of Formula I wherein A is selected from oxazolyl, isoxazolyl, dihydrofuryl, imidazolyl, and pyrazolyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

An even more preferred class of compounds which inhibit cyclooxygenase-2 consists of compounds of Formula I wherein A is selected from oxazolyl, isoxazolyl, imidazolyl, and pyrazolyl; wherein $R^1$ is phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

A family of specific compounds of particular interest within Formula I consists of compounds and pharmaceutically-acceptable salts thereof as follows:

4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(3-fluoro-4-methoxyphenyl)-3-(difluoromethyl)-1H-pyrazol-1-yl]benzenesulfonamide;

3-[1-[4-(methylsulfonyl)phenyl]-4-trifluoromethyl-1H-imidazol-2-yl]pyridine;

2-methyl-5-[1-[4-(methylsulfonyl)phenyl]-4-trifluoromethyl-1H-imidazol-2-yl]pyridine;

4-[2-(5-methylpyridin-3-yl)-4-(trifluoromethyl)-1H-imidazol-1-yl]benzenesulfonamide;

4-[5-methyl-3-phenylisoxazol-4-yl]benzenesulfonamide;

4-[5-hydroxyethyl-3-phenylisoxazol-4-yl]benzenesulfonamide;

[2-trifluoromethyl-5-(3,4-difluorophenyl)-4-oxazolyl]benzenesulfonamide;

4-[2-methyl-4-phenyl-5-oxazolyl]benzenesulfonamide; and

4-[5-(3-fluoro-4-methoxyphenyl-2-trifluoromethyl)-4-oxazolyl]benzenesulfonamide.

Preferred leukotriene $A_4$ hydrolase inhibitors include Rhone-Poulenc Rorer RP-64996 and compounds of Formula II $$Ar^1\text{-}Q\text{-}Ar^2\text{-}Y\text{-}R\text{-}Z \qquad (II)$$

or a pharmaceutically-acceptable salt thereof, and a pharmaceutically-acceptable carrier, wherein $Ar^1$ is an aryl moiety selected from:
(i) phenyl, mono-, di-, or tri-substituted phenyl with the substituents selected from Cl, Br, F, $CF_3$, lower alkyl, lower alkoxy, $NH_2$, $NO_2$ and OH;
(ii) 2-, 4- or 5-thiazolyl,
(iii) 2-, 3- or 4-pyridinyl,
(iv) 2- or 3-thienyl, and
(v) 2- or 3-furyl;

wherein $Ar^2$ is an aryl moiety selected from:

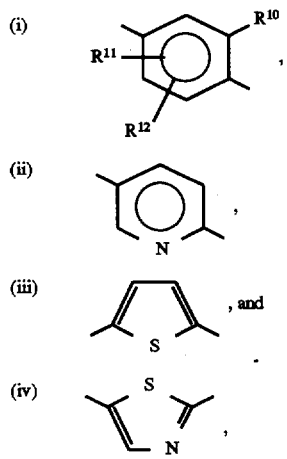

wherein

Q is selected from:
(i) —O—,
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

wherein

Y is selected from:
(i) —O—,
(ii) —S—, (iii) —NH—,
(iv) —S(O)—, and
(v) —S(O₂)—;

wherein

R is selected from:
(i) linear or branched $C_2$-$C_6$ alkylenyl; and
(ii) —$C(R^{13})(R^{14})$—$(CH_2)_m$—;

wherein

Z is selected from:

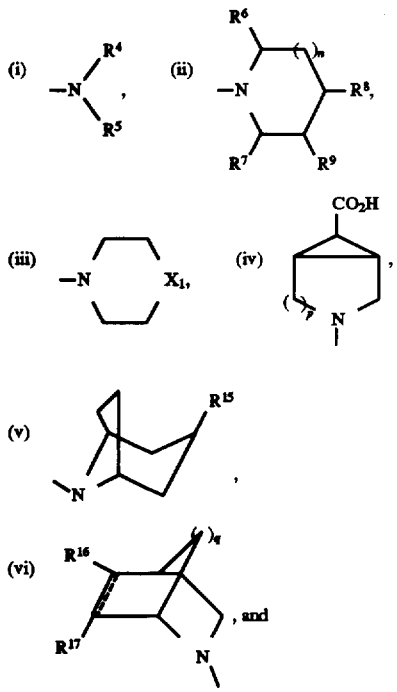

(viii) a monocyclic or bicyclic heteroaromatic moiety having at least one heteroatom, wherein the heteroatom is nitrogen, and wherein the monocyclic heteroaromatic moiety comprises a 5- or 6-membered ring and the bicyclic heteroaromatic moiety comprises a fused 9- or 10-membered ring;

wherein $R^4$ and $R^5$ are independently selected from:
(i) H,
(ii) lower alkyl or allyl,
(iii) benzyl,
(iv) —$(CH_2)_a COR^{18}$, (v) 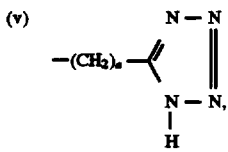

and
(vi) —$(CH_2)_a$—OH;

wherein $R^6$ and $R^7$ are independently H or lower alkyl;

wherein $R^8$ and $R^9$ are independently selected from (i) H
(ii) —OH, =O or —$(CH_2)_a$—OH,
(iii) —$(CH_2)_a COR^{18}$
(iv) —$(CH_2)_a CONH(CH_2)_b CO_2 R^{19}$,
(v) —$NHR^{20}$, (vi) 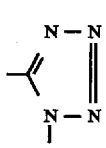

(vii) 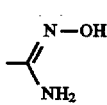

(viii) 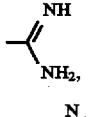

(ix) 

wherein $R^{10}$ is H, halogen, lower alkyl, lower alkoxy, nitro, or hydroxy, or $R^{10}$ taken together with $R^{13}$ is an alkylenyl group having one or two carbon atoms;

wherein $R^{11}$ and $R^{12}$ are independently H, halogen, lower alkyl, lower alkoxy, $NH_2$, $NO_2$ or OH;

wherein $R^{13}$ is H, or lower alkyl, or $R^{13}$ taken together with $R^{10}$ is an alkylenyl group having one or two carbon atoms;

wherein $R^{14}$ is H or lower alkyl;

wherein $R^{15}$ is selected from
(i) H,
(ii) —OH or =O,
(iii) —$(CH_2)_a COR^{18}$
(iv) —$(CH_2)_a CONH(CH_2)_b CO_2 R^{19}$, and
(v) —$NHR^{20}$;

wherein $R^{16}$ and $R^{17}$ are independently hydrogen, or —$(CH_2)_a COR^{18}$, provided that at least one of $R^{16}$ and $R^{17}$ is hydrogen;

wherein $R^{18}$ is —$OR^{19}$, —$NHR^{19}$ or —$NHNH_2$;

wherein $R^{19}$ is H, lower alkyl or benzyl;

wherein $R^{20}$ is H, lower alkyl, benzyl, —$COR^{19}$ or —$CONH_2$;

wherein $X^1$ is

—S—, or —O—, wherein $R^{21}$ is H, lower alkyl, —CONH$_2$, —CSNH$_2$, —COCH$_3$ or —SO$_2$CH$_3$;
wherein
a and b are independently integers of from 0 to 5;
wherein
m is 1, 2 or 3;
wherein
n is 0, 1, 2 or 3;
wherein
p is 1 or 2; and
wherein
q is 1, 2 or 3;
provided however that where R is —C($R^{13}$)($R^{14}$)—CH$_2$)$_m$—, and $R^{13}$ taken together with $R^{10}$ forms an alkylenyl group having one or two carbon atoms, then —Ar$^2$—Y—R— is

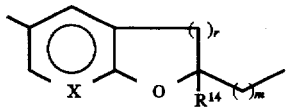

wherein

X is —CH— or —N—; and wherein r is 1 or 2; further provided that wherein Z is

and either $R^4$ or $R^5$, or both $R^4$ and $R^5$ are —(CH$_2$)$_a$COR$^{18}$, then a is not 0.

More preferred leukotriene A$_4$ hydrolase inhibitors include compounds of Formula II wherein Ar$^1$—Q—Ar$^2$—Y— is

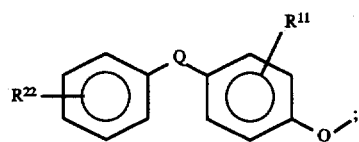

wherein

Q is —O—, —CH$_2$—, —CF$_2$— or —CH$_2$O—; and $R^{11}$ and $R^{22}$ are independently H, lower alkyl, lower alkoxy, halogen, NH$_2$ or NO$_2$.

Other more preferred 5-lipoxygenase inhibitors include leukotriene A$_4$ hydrolase inhibitors include compounds of Formula II wherein Ar$^1$—Q—AR$^2$—Y— is

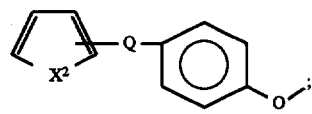

wherein $X^2$ is —S—, or —CH=N—; and wherein Q is —CH$_2$—, —CF$_2$—, —O— or —CH$_2$O—.

A family of specific compounds of particular interest within Formula II consists of compounds and pharmaceutically-acceptable salts thereof in Table A:

TABLE A

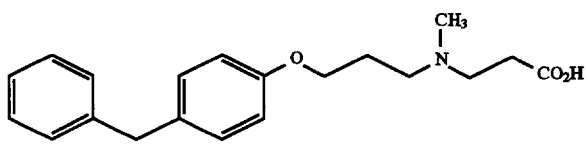

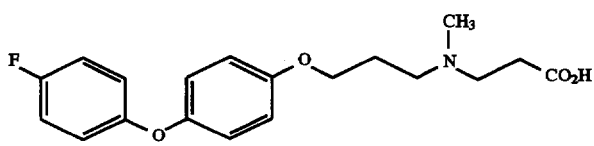

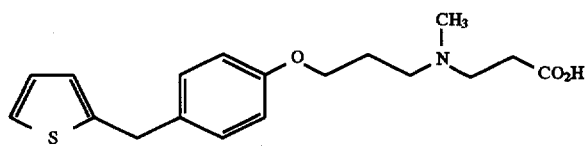

-continued
TABLE A

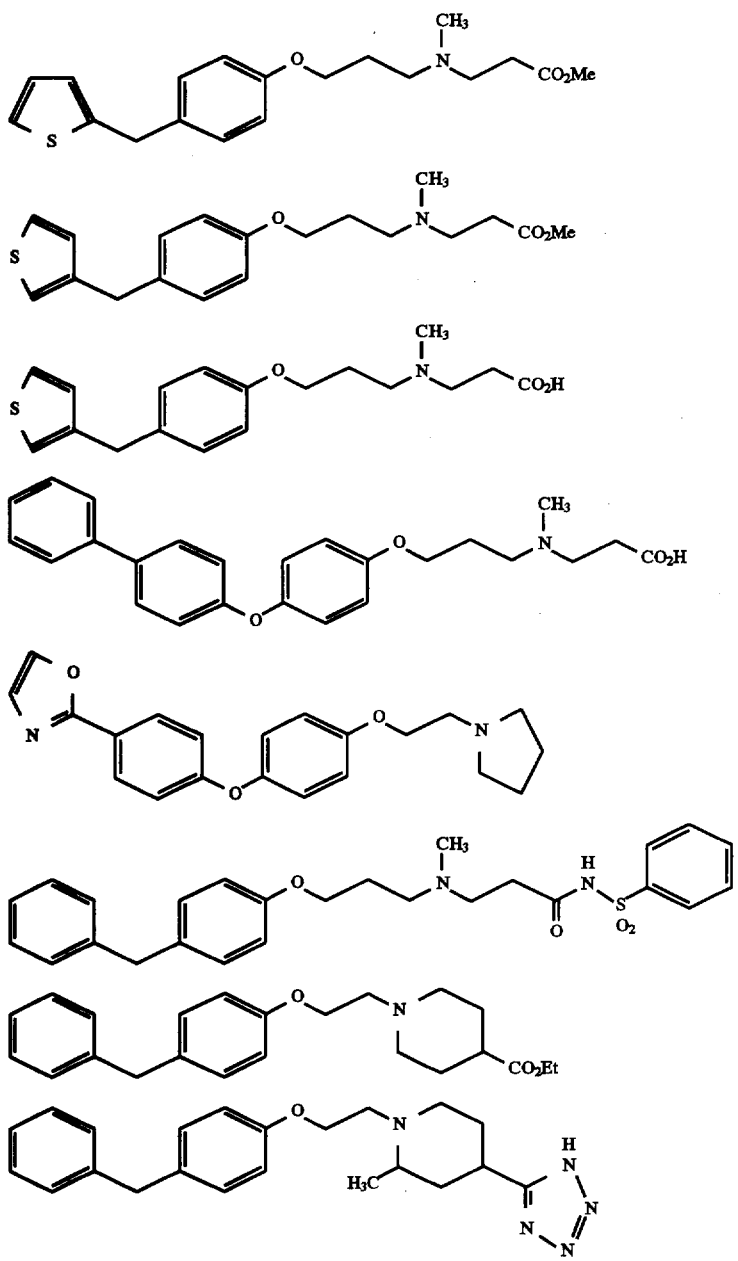

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alk-enyl" embraces linear or branched radicals having at least one carbon-carbon double bond of two to about twenty carbon atoms or, preferably, one to about twelve carbon atoms. More preferred alkyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclo" embraces saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of unsaturated heterocyclo radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4- thiadiazolyl, 1,3,4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term also embraces radicals where heterocyclo radicals are fused with aryl radicals. Examples of such fused bicyclic radicals include benzofuran, benzothiophene, and the like. Said "heterocyclo group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote $NH_2O_2S$—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —$CO_2H$. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include substituted or unsubstituted methylcarbonyl, ethylcarbonyl, phenylcarbonyl and benzylcarbonyl. The term "aralkyl" embraces arylsubstituted alkyl radicals such as benzyl, diphenylmethyl, triphenylmethyl, phenylethyl, and diphenylethyl. The aryl in said aralkyl may be additionally substituted with halo, alkyl, alkoxy, haloalkyl and haloalkoxy. The terms benzyl and phenylmethyl are interchangeable. The term "heterocycloalkyl" embraces saturated and partially unsaturated heterocyclo-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, haloalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl. The term "aminocarbonyl" denotes an amide group of the formula —C(=O)$NH_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

The present invention comprises a pharmaceutical composition comprising a therapeutically-effective amount of a leukotriene $A_4$ hydrolase inhibitor and a cyclooxygenase-2 inhibitor compound of Formula I in association with at least one pharmaceutically-acceptable carrier, adjuvant or diluent.

The present invention also comprises a method of treating inflammation or inflammation-associated disorders in a subject, the method comprising administering to the subject having or susceptible to such inflammation or disorder a therapeutically-effective amount of a leukotriene $A_4$ hydrolase inhibitor and a cyclooxygenase-2 inhibitor compound of Formula I. The method of the present invention also includes prophylactic or chronic treatment, especially in the case of arthritis and other inflammatory conditions which can lead to deterioration in the joints.

Also included in the family of compounds of Formulas I–II are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I–II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formulas I–II include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the methylglucamine) and procaine. All of these salts may be prepared by conventional means from the corresponding compound of Formulas I–II by reacting, corresponding compound of Formulas I–II by reacting, for example, the appropriate acid or base with the compound of Formulas I–II.

GENERAL SYNTHETIC PROCEDURES

The compounds of the invention can be synthesized according to the following procedures of Schemes I–XII, wherein the substituents are as defined for Formulas I–II, above, except where further noted.

Scheme I

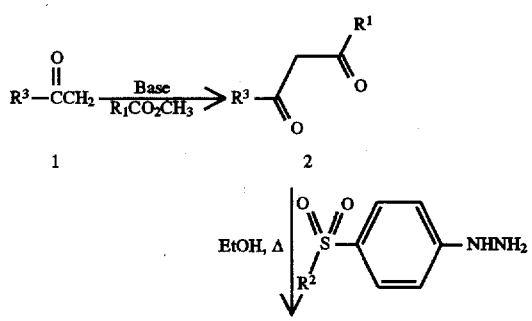

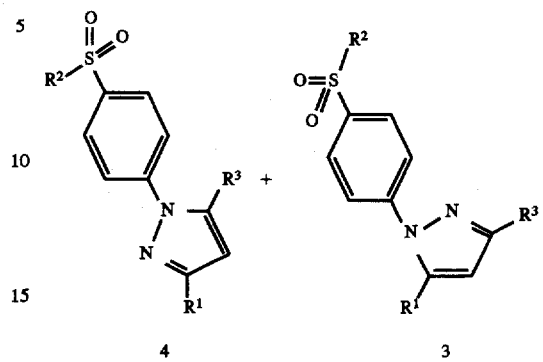

Synthetic Scheme I shows the preparation of cyclooxygenase-2 inhibitor compounds, as described in U.S. patent application Ser. No. 08/223,629, which is incorporated by reference, embraced by Formula I where R is Ar or Z (as defined in Scheme I), and $R^a$ is a radical defined above for the substituents optionally substituted on A. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 4,146,721, 5,051,518, 5,134,142 and 4,914,121 which also are incorporated by reference.

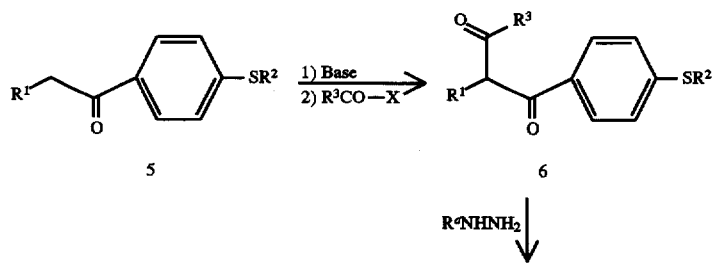

-continued
Scheme II

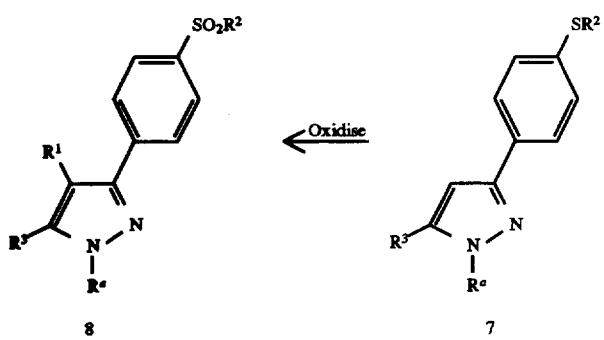

Scheme II shows the four step procedure for forming cyclooxygenase-2 inhibitor pyrazoles 8 as described in U.S. patent application Ser. No. 08/278,297 (where $R^a$ is alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer.

The desired pyrazole 8, usually a white or pale yellow solid, is obtained in pure form either by chromatography or recrystallization.

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

Scheme III

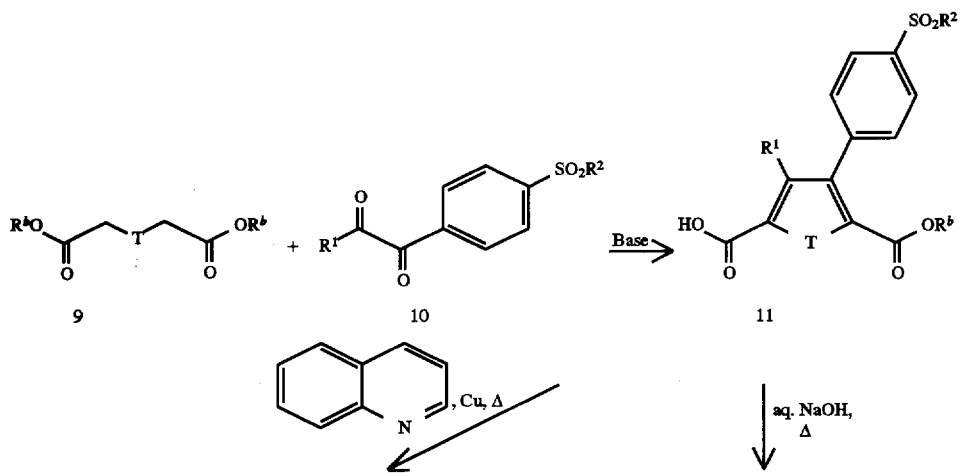

Scheme III
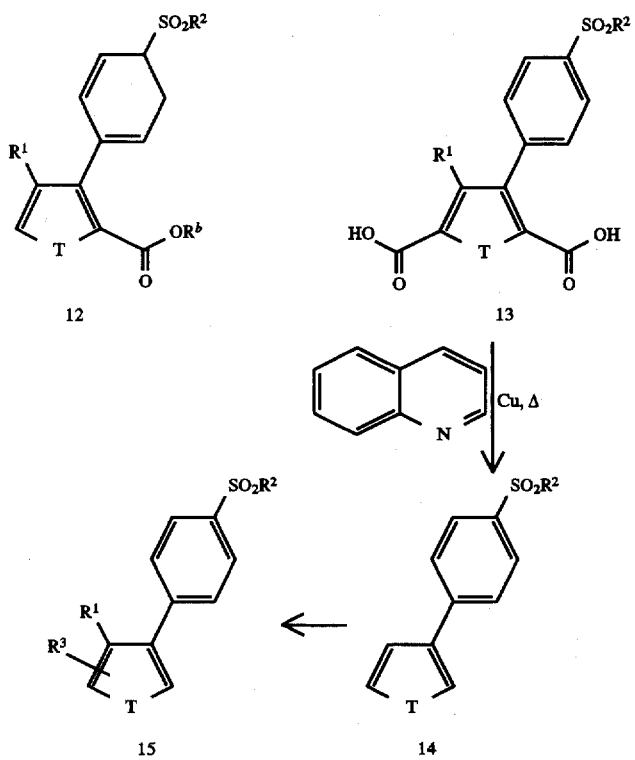
Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.
Scheme IV
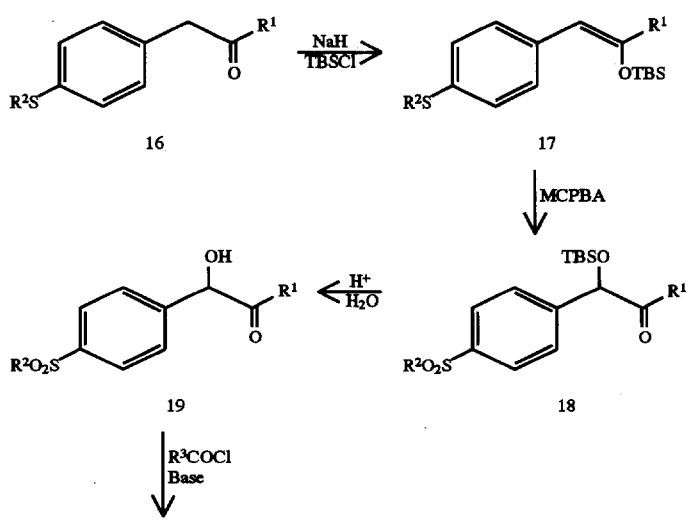

-continued
Scheme IV

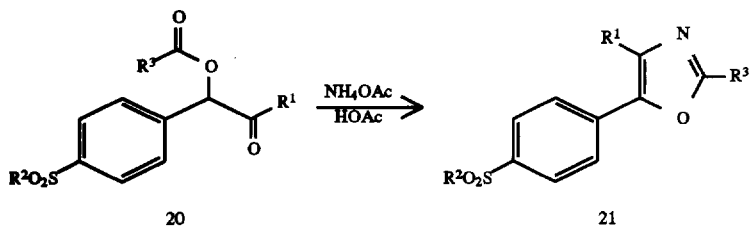

Cyclooxygenase-2 inhibitor diaryl/heteroaryl oxazoles can be prepared by the methods described in U.S. Pat. Nos. 3,743,656, 3,644,499 and 3,647,858, and PCT documents WO 95/00501 and WO94/27980, which are incorporated by reference.

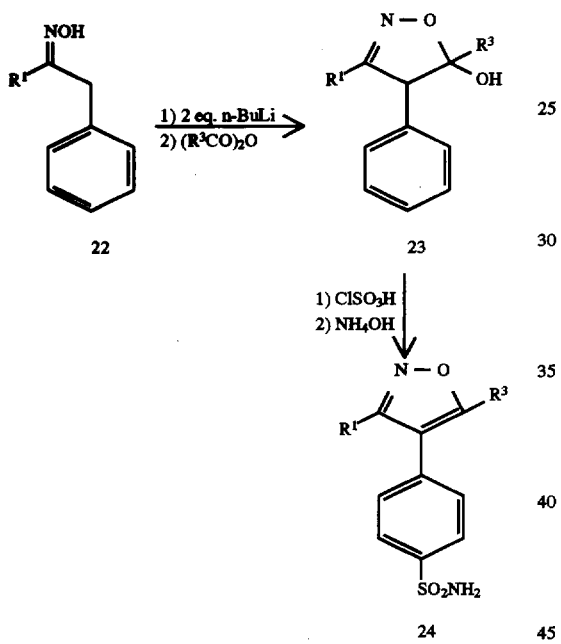

Cyclooxygenase-2 inhibitor diaryl/heteroaryl isoxazoles can be prepared by the methods described in U.S. application Ser. No. 08/387,680, PCT documents WO92/05162, and WO92/19604, and European Publication EP 26928 which are incorporated by reference. Sulfonamides 24 can be formed from the hydrated isoxazole 23 in a two step procedure. First, hydrated isoxazole 23 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 24.

Scheme VI

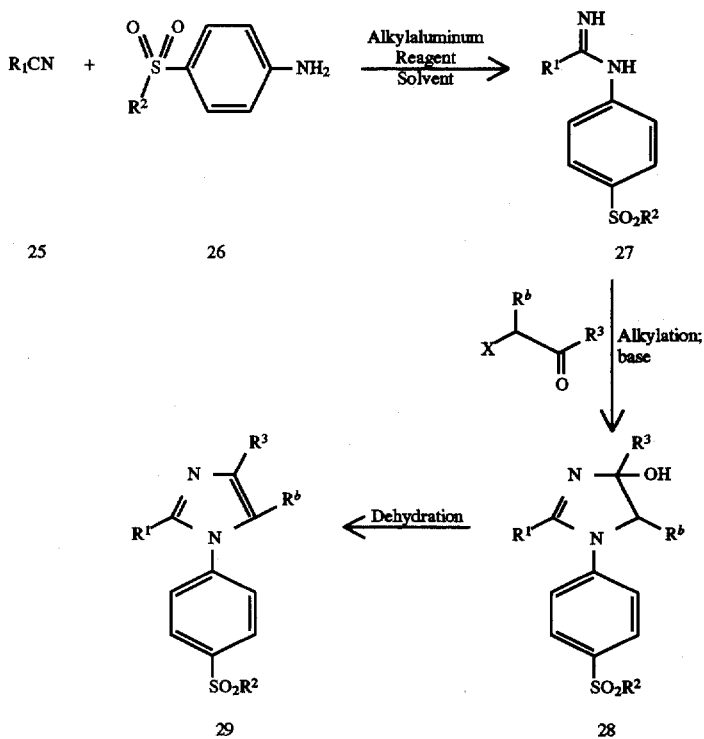

Scheme VI shows the three step preparation of the cyclooxygenase-2 inhibitor imidazoles 29 of the present invention. In step 1, the reaction of substituted nitriles ($R^1CN$) 25 with primary phenylamines 26 in the presence of alkylaluminum reagents such as trimethylaluminum, triethylaluminum, dimethylaluminum chloride, diethylaluminum chloride in the presence of inert solvents such as toluene, benzene, and xylene, gives amidines 27. In step 2, the reaction of amidine 27 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 28 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 28 may be dehydrated in the presence of an acid catalyst such as 4-toluenesulfonic acid or mineral acids to form the 1,2-disubstituted imidazoles 29 of the invention. Suitable solvents for this dehydration step are e.g., toluene, xylene and benzene. Trifluoroacetic acid can be used as solvent and catalyst for this dehydration step.

In some cases (e.g., where YR=methyl or phenyl) the intermediate 28 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. No. 4,822,805, U.S. application Ser. No. 08/282,395 and PCT document WO 93/14082, which are incorporated by reference.

Scheme VII

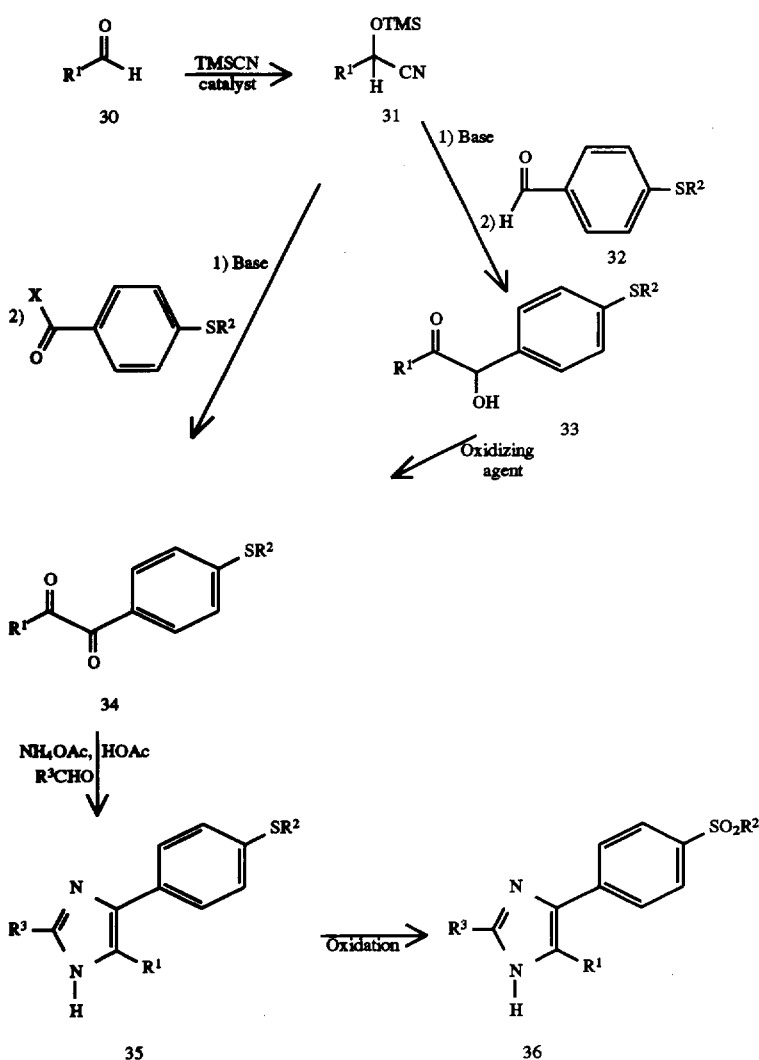

The subject imidazole cyclooxygenase-2 inhibitor compounds 36 of this invention may be synthesized according to the sequence outlined in Scheme VII. Aldehyde 30 may be converted to the protected cyanohydrin 31 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 31 with a strong base followed by treatment with benzaldehyde 32 (where $R^2$ is alkyl) and using both acid and base treatments, in that order, on workup gives benzoin 33. Examples of strong bases suitable for this reaction are lithium diisopropylamide (LDA) and lithium hexamethyldisilazane. Benzoin 33 may be converted to benzil 34 by reaction with a suitable oxidizing agent, such as bismuth oxide or manganese dioxide, or by a Swern oxidation using dimethyl sulfoxide (DMSO) and trifluoroacetic anhydride. Benzil 34 may be obtained directly by reaction of the anion of cyanohydrin 31 with a substituted benzoic acid halide. Any of compounds 33 and 34 may be used as intermediates for conversion to imidazoles 35 (where $R^2$ is alkyl) according to chemical procedures known by those skilled in the art and described by M. R. Grimmett, "Advances in Imidazole Chemistry" in Advances in Heterocyclic Chemistry, 12, 104 (1970). The conversion of 34 to imidazoles 35 is carried out by reaction with ammonium acetate and an appropriate aldehyde (RYCHO) in acetic acid. Benzoin 36 may be converted to imidazoles 38 by reaction with formamide. In addition, benzoin 36 may be converted to imidazoles by first acylating with an appropriate acyl group (RYCO—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, U.S. application Ser. No. 08/281,903 European publication EP 372,445, and PCT document WO 95/00501, which are incorporated by reference.

Scheme VIII

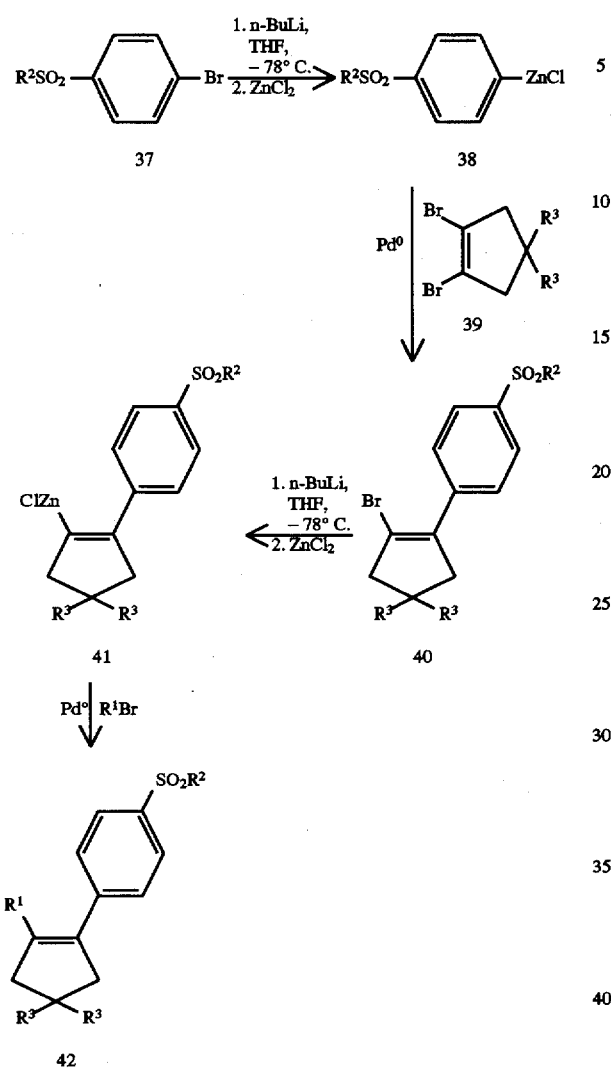

Diaryl/heteroaryl cyclopentene cyclooxygenase-2 inhibitors can be prepared by the methods described in U.S. Pat. No. 5,344,991, and PCT document WO 95/00501, which are incorporated by reference.

Scheme IX

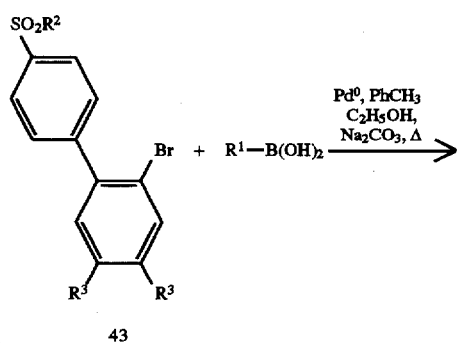

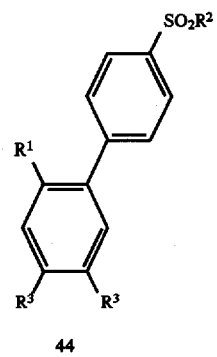

Similarly, Synthetic Scheme IX shows the procedure for the preparation of 1,2-diarylbenzene cyclooxygenase-2 inhibitor agents 44 from 2-bromobiphenyl intermediates 43 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 43 are reacted with the boronic acids in toluene/ethanol at reflux in the presence of a Pd° catalyst, e.g., tetrakis (triphenylphosphine)palladium(0), and 2M sodium carbonate to give the corresponding 1,2-diarylbenzene antiinflammatory agents 44 of this invention. Such terphenyl compounds can be prepared by the methods described in U.S. application Ser. No. 08/346,433, which is incorporated by reference.

Scheme X

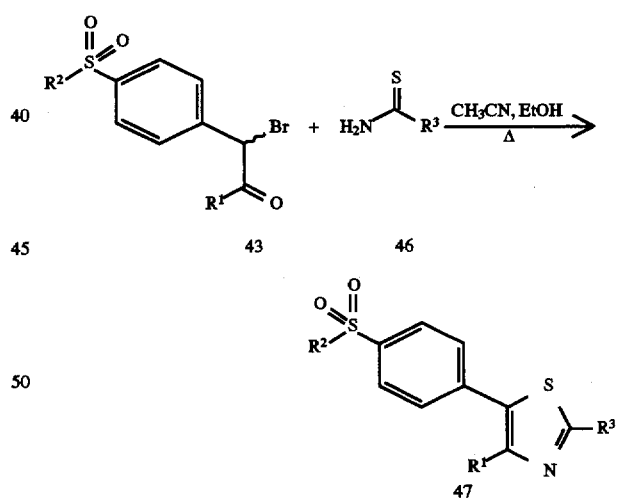

Diaryl/heteroaryl thiazole cyclooxygenase-2 inhibitors can be prepared by the methods described in U.S. Pat. No. 4,051,250, 4,632,930, U.S. application Ser. No. 08/281,288, European Application EP 592,664, and PCT document WO 95/00501, which are incorporated by reference. Isothiazoles can be prepared as described in PCT document WO 95/00501. Diaryl/heteroaryl pyridine cyclooxygenase-2 inhibitors can be prepared by the methods described in U.S. Pat. Nos. 5,169,857, 4,011,328, 4,533,666, U.S. application Ser. No. 08/386,843 and U.S. application Ser. No. 08/387, 150 which are incorporated by reference.

Scheme XI

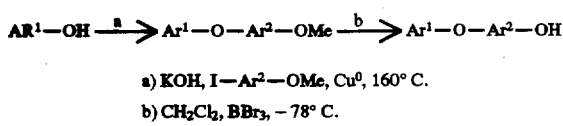

a) KOH, I—Ar²—OMe, Cu⁰, 160° C.
b) CH₂Cl₂, BBr₃, −78° C.

Scheme XI shows a general method for the preparation of phenols of the formula Ar¹—O—Ar²—OH wherein Ar¹ is a substituted arylphenol. Ar¹ may be any substituted arylphenol which is capable of reacting with 4-iodoanisole in an Ullman coupling reaction. See, A. Moroz, et al., *Russ. Chem. Rev.* 43,679 (1974). The Ullman reaction is carried out conventionally in the presence of activated copper or copper iodide at a temperature of about 150° C. to 200° C. A particularly preferred substituted phenol for providing compounds of the present invention having a substituted Ar¹ moiety is 4-fluorophenol.

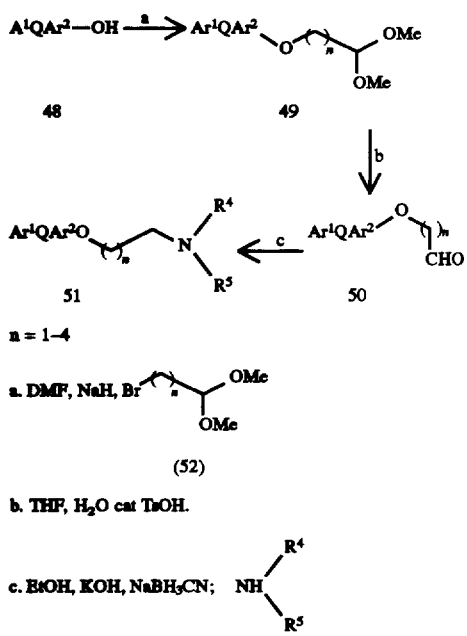

Scheme XII describes yet another method for preparation of compounds of Formula II in which compound 48 is alkylated with a bromodimethyl acetal 52 in DMF in the presence of NaH to afford acetal 49. Subsequent deprotection with toluene-4-sulfonic acid in THF/H₂O affords intermediate aldehyde 50 which is reductively aminated [EtOH, KOH, NaBH₃CN] with an amine of the formula HNR⁴R⁵ to afford compound 51 which is a compound of Formula II.

The leukotriene A₄ hydrolase inhibitor compounds of Formula II can be synthesized according to the other methods described in U.S. patent application Ser. No. 08/321,184 which is incorporated by reference.

The following examples contain detailed descriptions of the methods of preparation of combinations with compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

BIOLOGICAL EVALUATION

A combination therapy of a cyclooxygenase-2 inhibitor and a leukotriene A₄ hydrolase inhibitor was evaluated as described in the following tests.

EXAMPLE 1

4-[5-(4-Chlorophenyl)-3-(trifluoromethyl)-1H-pyrazol-1-yl]benzenesulfonamide

Step 1

Preparation of 4,4,4-trifluoro-1-[4-(chloro)phenyl]-butane-1,3-dione

Ethyl trifluoroacetate (23.52 g, 166 mmol) was dissolved in methyl tert-butyl ether (75 mL). To the stirred solution was added 25 weight % sodium methoxide (40 mL, 177 mmol). Next 4'-chloroacetophenone (23.21 g, 150 mmol) was dissolved in methyl tert-butyl ether (20 mL), and added to the reaction dropwise. After stirring overnight (15.75 hours), 3N HCl (70 mL) was added. The organic layer was collected, washed with brine (75 mL), dried over MgSO₄, filtered, and concentrated in vacuo to give a 35.09 g of yellow-orange solid. The solid was recrystallized from isooctane to give 31.96 g, 85% of the dione, mp 66°–67° C.

Step 2

Preparation of 4-[5-(4-chlorophenyl)-3-(trifluoromethyl)-1H-pyrazol-1-yl]benzenesulfonamide 4-Sulphonamidophenyl hydrazine hydrochloride (982 mg, 4.4 mmol 1.1 equivalent) was added to a stirred solution of 4,4,4-trifluoro-1-[4-(chloro)phenyl]-butane-1,3-dione (1.00 g, 4.0 mmol) in ethanol (50 mL). The reaction was heated to reflux and stirred for 20 hours. After cooling to room temperature, the reaction mixture was concentrated in vacuo. The residue was taken up in ethyl acetate and washed with water and brine and dried over MgSO₄, filtered, and concentrated in vacuo to give a light brown solid which was recrystallized from ethyl acetate and isooctane to give the pyrazole (1.28 g, 80%): mp 143°–145° C.; EI GC-MS M+=401.

EXAMPLE 2

4-[5-(3-Fluoro-4-methoxyphenyl)-3-(difluoromethyl)-1H-pyrazol-1-yl]benzenesulfonamide Step 1

Preparation of 3'-fluoro-4'-methoxy-acetophenone

Acetyl chloride (51.0 g, 0.65 mol) was added dropwise to a stirred solution of aluminum chloride (80.0 g, 0.6 mol) and chloroform (750 mL), maintaining the temperature between 5°–10° C. The mixture was stirred for 10 minutes at 5° C. before the dropwise addition of 2-fluoroanisole (62.6 g, 0.5 mol). The mixture was stirred at 0°–10° C. for 1 hour and poured into ice (1 L). The resultant layers were separated and the aqueous layer was extracted with dichloromethane (2×250 mL). The combined organic layers were washed with water (2×150 mL), dried over anhydrous MgSO₄, filtered and concentrated in vacuo to a volume of 300 mL. Hexanes were added and a white solid formed which was isolated by filtration and air dried. This material was recrystallized from a mixture of dichloromethane and hexanes to afford (77.2 g, 92%) of material suitable for use in the next step: mp 92°–94° C.

Step 2
Preparation of 4,4-difluoro-1-(3-fluoro-4-methoxyphenyl)-butane-1,3-dione Ethyl difluoroacetate (4.06 g, 32.7 mmol) was dissolved in methyl t-butyl ether (50 mL). To the stirred solution was added 25 weight % sodium methoxide (7.07 g, 32.7 mmol) followed by 3'-fluoro-4'-methoxyacetophenone (5.0 g, 29.7 mmol). After stirring for 16 hours, 1N HCl (50 mL) was added. The organic layer was collected and washed with water (2×50 mL), dried over anhydrous $MgSO_4$, filtered, and added to hexanes to precipitate a tan solid (7.0 g, 96%): mp 70°–72° C.

Step 3
Preparation of 4-[5-(3-fluoro-4-methoxyphenyl)-3-(difluoromethyl)-1H-pyrazol-1-yl]benzenesulfonamide 4,4-Difluoro-1-(3-fluoro-4-methoxyphenyl)-butane-1,3-dione from Step 2 (7.0 g, 28.4 mmol) was dissolved in ethanol (150 mL). To the stirred mixture was added 4-sulphonamidophenyl hydrazine hydrochloride (7.4 g, 33 mmol) and stirred at reflux overnight (16 hours). The mixture was cooled and water was added until crystals slowly appeared. The product was isolated by filtration and air dried to provide the desired product as a light tan solid (9.8 g, 87%): mp 159°–161° C.; Anal. Calc'd. for $C_{17}H_{14}N_3SO_3F_3$: C, 51.38; H, 3.55; N, 10.57. Found: C, 51.46; H, 3.52; N, 10.63.

EXAMPLE 3

3-[Methyl[3-[(4-phenylmethyl)phenoxy]propyl]-amino]propanoic acid

3-[Methyl[3-[4-phenylmethyl)phenoxy]propyl]-amino] propanoic acid is prepared by a four step method. 4-Hydroxydiphenylmethane is alkylated with 3-chlorobromopropane at 70° C. in the presence of potassium carbonate for 16 hours to form the 1-chloro-3-[4-phenylmethyl)phenoxy]propane. The chloropropane is condensed with methylamine at 60° C. in a Parr bomb at 200 psi for 20 hours. The secondary amine is isolated as the hydrochloride salt. Condensation of the secondary amine with benzyl acetate in ethanol at room temperature for 3 hours affords the β-amino acid derivative. The derivative is directly hydrogenated (Pd/C, $H_2$, ethanol, 2 psi) to afford 3-[methyl[3-[4-phenylmethyl)phenoxy]propyl]-amino] propanoic acid.

Induction and assessment of collagen induced arthritis in mice

Arthritis was induced in 8–12 week old male DBA/1 mice by injection of 50 μg of chick type II collagen (CII) (provided by Dr. Marie Griffiths, Univ. of Utah, Salt Lake City, Utah) in complete Freunds adjuvant (Sigma) on day 0 at the base of the tail as previously described [J. Stuart, *Annual Rev. Immunol.*, 2, 199 (1984)]. Compounds were prepared as a suspension in 0.5% methylcellulose (Sigma, St. Louis, Mo.), 0.025% Tween 20 (Sigma). The cyclooxygenase-2 inhibitors (Example 1 and 2) and the leukotriene $A_4$ hydrolase inhibitor (Example 3) were administered alone or a cyclooxygenase-2 inhibitor and the leukotriene $A_4$ hydrolase inhibitor in combination. The compounds were administered in non-arthritic animals by gavage in a volume of 0.1 ml beginning on day 20 post collagen injection and continuing daily until final evaluation on day 55. Animals were boosted on day 21 with 50 μg of collagen (CII) in incomplete Freunds adjuvant. The animals were subsequently evaluated several times each week for incidence and severity of arthritis until day 56. Any animal with paw redness or swelling was counted as arthritic.

Scoring of severity was carried out using a score of 0–3 for each paw (maximal score of 12/mouse) as previously described [P. Wooley, et al., *Trans. Proc.*, 15, 180 (1983)]. The animals were measured for incidence of arthritis and severity in the animals where arthritis was observed. The incidence of arthritis was determined at a gross level by observing the swelling or redness in the paw or digits. Severity was measured with the following guidelines. Briefly, animals displaying four normal paws, i.e., no redness or swelling were scored 0. Any redness or swelling of digits or the paw were scored as 1. Gross swelling of the whole paw or deformity was scored as 2. Ankylosis of joints was scored as 3. Results are shown in Tables I–II.

Histological Examination of Paws

In order to verify the gross determination of a non-arthritic animal, a histological examination was performed. Paws from animals sacrificed at the end of the experiment were removed, fixed and decalcified as previously described [R. Jonsson, *J. Immunol. Methods*, 88, 109 (1986)]. Samples were paraffin embedded, sectioned, and stained with hematoxylin and eosin by standard methods. Stained sections were examined for cellular infiltrates, synovial hyperplasia, and bone and cartilage erosion.

TABLE 1

Incidence of collagen induced arthritis

| Example | Exp. #1[a] Incidence (%) | Exp. #2[b] Incidence (%) |
|---|---|---|
| Vehicle | 88% | 100% |
| 1 (COX-2) |  | 67% |
| 2 (COX-2) | 88% |  |
| 3 (LTA4) | 78% | 80% |
| COX-2 + LTA4 |  |  |
| 2 + 3 | 67% |  |
| 1 + 3 |  | 17% |

TABLE 2

Severity of collagen-induced arthritis

| Example | Exp. #1[a] Severity | Exp. #2[b] Severity |
|---|---|---|
| Vehicle | 5.76 ± 91 | 4.42 ± 59 |
| 1 (COX-2) |  | 1.58 ± 40 |
| 2 (COX-2) | 3.38 ± 62 |  |
| 3 (LTA4) | 2.89 ± 92 | 3.00 ± 55 |
| COX-2 + LTA4 |  |  |
| 2 + 3 | 1.44 ± 41 |  |
| 1 + 3 |  | 0.42 ± 28 |

EXAMPLE 4

A formulation is prepared having the following components:

700 mg of a cyclooxygenase-2 inhibitor and 700 mg of an $LTA_4$ hydrolase inhibitor.

EXAMPLE 5

A formulation is prepared having the following components:

350 mg of 4-[5-(3-fluoro-4-methoxyphenyl)-3-(difluoromethyl)-1H-pyrazol-1-yl]benzenesulfonamide and 350 mg of 3-[methyl[3-[4-phenylmethyl)phenoxy] propyl]-amino]propanoic acid.

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered ORALLY, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A pharmaceutical composition comprising a therapeutically-effective amount of a cyclooxygenase-2 inhibitor selected from N-2-cyclohexyloxy-4-nitrophenyl) methanesulfonamide, meloxicam, flosulide and compounds of Formula I

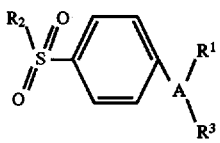   I wherein

A is a 5- or 6-member ring substituent selected from partially unsaturated or unsaturated heterocyclo and carbocyclic rings;

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl, and amino; and wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof;

and a leukotriene $A_4$ hydrolase inhibitor selected from compounds of Formula II

   (II)

or a pharmaceutically-acceptable salt thereof, and a pharmaceutically-acceptable carrier, wherein $Ar^1$ is an aryl moiety selected from:
(i) phenyl, mono-, di-, or tri-substituted phenyl with the substituents selected from Cl, Br, F, $CF_3$, lower alkyl, lower alkoxy, $NH_2$, $NO_2$ and OH;
(ii) 2-, 4- or 5-thiazolyl,
(iii) 2-, 3- or 4-pyridinyl,
(iv) 2- or 3-thienyl, and
(v) 2- or 3-furyl;

wherein $Ar^2$ is an aryl moiety selected from:

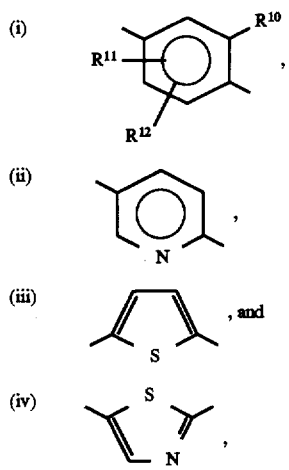

wherein

Q is selected from:
(i) —O—,
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

wherein

Y is selected from:
(i) —O—,
(ii) —S—,
(iii) —NH—,
(iv) —S(O)—, and
(v) —$S(O_2)$—;

wherein

R is selected from:
(i) linear or branched $C_2$-$C_6$ alkylenyl; and
(ii) —$C(R^{13})$ ($R^{14}$)—$(CH_2)_m$—;

wherein

Z is selected from:

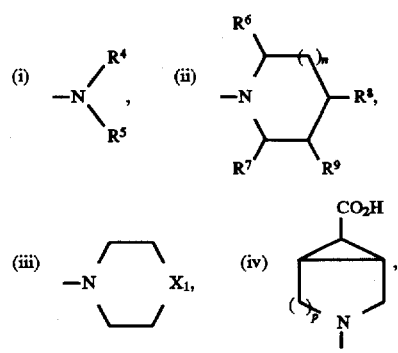

(v) 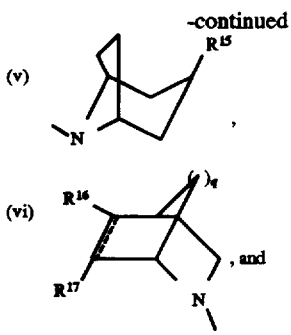

(vi) 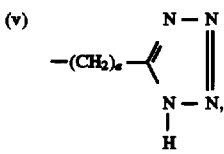, and (viii) a monocyclic or bicyclic heteroaromatic moiety having at least one heteroatom, wherein the heteroatom is nitrogen, and wherein the monocyclic heteroaromatic moiety comprises a 5- or 6-membered ring and the bicyclic heteroaromatic moiety comprises a fused 9- or 10-membered ring;

wherein $R^4$ and $R^5$ are independently selected from:
(i) H,
(ii) lower alkyl or allyl,
(iii) benzyl,
(iv) —$(CH_2)_a COR^{18}$, (v) 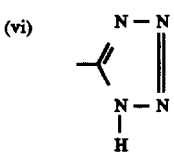

and
(vi) —$(CH_2)_a$—OH;

wherein $R^6$ and $R^7$ are independently H or lower alkyl;

wherein $R^8$ and $R^9$ are independently selected from (i) H
(ii) —OH, =O or —$(CH_2)_a$—OH,
(iii) —$(CH_2)_a COR^{18}$
(iv) —$(CH_2)_a CONH(CH_2)_b CO_2 R^{19}$,
(v) —$NHR^{20}$, (vi) 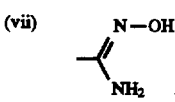

(vii) 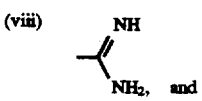

(viii) 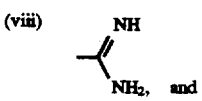, and (ix) 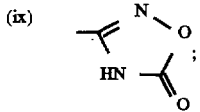;

wherein $R^{10}$ is H, halogen, lower alkyl, lower alkoxy, nitro, or hydroxy, or $R^{10}$ taken together with $R^{13}$ is an alkylenyl group having one or two carbon atoms;

wherein $R^{11}$ and $R^{12}$ are independently H, halogen, lower alkyl, lower alkoxy, $NH_2$, $NO_2$ or OH;

wherein $R^{13}$ is H, or lower alkyl, or $R^{13}$ taken together with $R^{10}$ is an alkylenyl group having one or two carbon atoms;

wherein $R^{14}$ is H or lower alkyl;

wherein $R^{15}$ is selected from
(i) H,
(ii) —OH or =O,
(iii) —$(CH_2)_a COR^{18}$
(iv) —$(CH_2)_a CONH (CH_2)_b CO_2 R^{19}$, and
(iv) —$NHR^{20}$;

wherein $R^{16}$ and $R^{17}$ are independently hydrogen, or —$(CH_2)_a COR^{18}$, provided that at least one of $R^{16}$ and $R^{17}$ is hydrogen;

wherein $R^{18}$ is —$OR^{19}$, —$NHR^{19}$ or —$NHNH_2$;

wherein $R^{19}$ is H, lower alkyl or benzyl;

wherein $R^{20}$ is H, lower alkyl, benzyl, —$COR^{19}$ or —$CONH_2$;

wherein $X^1$ is

—S—, or —O—, wherein $R^{21}$ is H, lower alkyl, —$CONH_2$, —$CSNH_2$, —$COCH_3$ or —$SO_2CH_3$;

wherein a and b are independently integers of from 0 to 5;

wherein m is 1, 2 or 3;

wherein n is 0, 1, 2 or 3;

wherein p is 1 or 2; and wherein q is 1, 2 or 3;

provided however that where R is —$C(R^{13})(R^{14})$—$CH_2)_m$—, and $R^{13}$ taken together with $R^{10}$ forms an alkylenyl group having one or two carbon atoms, then —$Ar^2$—Y—R— is

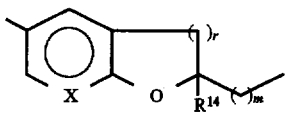

wherein

X is —CH— or —N—; and wherein r is 1 or 2; further provided that wherein Z is

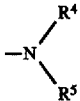

and either $R^4$ or $R^5$, or both $R^4$ and $R^5$ are —$(CH_2)_aCOR^{18}$, then a is not 0.

2. The pharmaceutical composition of claim 1 wherein the leukotriene $A_4$ hydrolase inhibitor is selected from compounds of Formula II wherein $Ar^1$—Q—$Ar^2$—Y— is

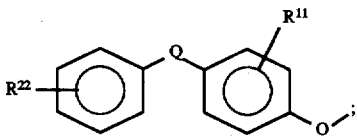

wherein

Q is —O—, —$CH_2$—, —$CF_2$— or —$CH_2O$—; and $R^{11}$ and $R^{22}$ are independently H, lower alkyl, lower alkoxy, halogen, $NH_2$ or $NO_2$.

3. The pharmaceutical composition of claim 1 wherein the leukotriene $A_4$ hydrolase inhibitor is selected from compounds of Formula II wherein $Ar^1$—Q—$AR^2$—Y— is

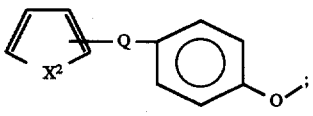

wherein $X^2$ is —S—, or —CH=N—; and wherein Q is —$CH_2$—, —$CF_2$—, —O— or —$CH_2O$—.

4. The pharmaceutical composition of claim 1, wherein the leukotriene $A_4$ hydrolase inhibitor is selected from compounds, their prodrugs and their pharmaceutically-acceptable salts, of the group consisting of ethyl-1-[2-[4-(phenylmethyl)phenoxy]ethyl]-4-piperidine-carboxylate;

1-[2-[4-(phenylmethyl)phenoxy]ethyl]-2-methyl-4-tetrazolylpiperidine;

1-[2-[4-(4-(2-oxazolyl)phenoxy)phenoxy]ethyl] pyrrolidine;

3-[methyl[3-[4-(2-thienylmethyl)phenoxy]propyl]amino] propanoic acid;

methyl-3-[methyl[3-[4-(2-thienylmethyl)phenoxy] propyl]amino]propanoate;

3-[methyl[3-[4-(3-thienylmethyl)phenoxy]propyl]amino] propanoic acid;

methyl-3-[methyl[3-[4-(3-thienylmethyl)phenoxy] propyl]amino]propanoate;

3-[methyl[3-[4-(phenylmethyl)phenoxy]propyl]amino] propanoic acid;

3-[methyl[3-[4-(4-fluorophenoxy)phenoxy]propyl] amine]propanoic acid; and

3-[methyl[3-[4-(4-biphenyloxy)phenoxy]propyl]amino] propanoic acid.

5. The pharmaceutical composition of claim 1 wherein A is selected from oxazolyl, isoxazolyl, thienyl, dihydrofuryl, furyl, pyrrolyl, pyrazolyl, thiazolyl, imidazolyl, isothiazolyl, cyclopentenyl, phenyl, and pyridyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^3$ is a radical selected from halo, lower alkyl, oxo, cyano, carboxyl, lower cyanoalkyl, heteroaryloxy, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, heteroaryloxy, alkoxycarbonyl, aminocarbonyl, alkylaminocarbonyl, alkylamino, aminoalkyl, alkylaminoalkyl, aryloxy, and aralkoxy; or a pharmaceutically-acceptable salt thereof.

6. The pharmaceutical composition of claim 5 wherein A is selected from oxazolyl, isoxazolyl, dihydrofuryl, imidazolyl, and pyrazolyl; wherein $R^1$ is selected from 5- and 6-membered heterocyclo, and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl lower carboxyalkyl lower cyanoalkyl halo, lower alkyl, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

7. The pharmaceutical composition of claim 6 wherein A is selected from oxazolyl, isoxazolyl, imidazolyl, and pyrazolyl; wherein $R^1$ is phenyl optionally substituted at a substitutable position with one or more radicals selected from methyl, ethyl, isopropyl, butyl, tert-butyl, isobutyl, pentyl, hexyl, trifluoromethyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

8. The pharmaceutical composition of claim 7, wherein the leukotriene A4 hydrolase inhibitor is selected from compounds, their prodrugs and their pharmaceutically-acceptable salts, of the group consisting of 4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(3-fluoro-4-methoxyphenyl)-3-(difluoromethyl)-1H-pyrazol-1-yl]benzenesulfonamide;

3-[1-[4-(methylsulfonyl)phenyl]-4-trifluoromethyl-1H-imidazol-2-yl]pyridine;

2-methyl-5-[1-[4-(methylsulfonyl)phenyl]-4-trifluoromethyl-1H-imidazol-2-yl]pyridine;

4-[2-(5-methylpyridin-3-yl)-4-(trifluoromethyl)-1H-imidazol-1-yl]benzenesulfonamide;

4-[5-methyl-3-phenylisoxazol-4-yl]benzenesulfonamide;

4-[5-hydroxyethyl-3-phenylisoxazol-4-yl]benzenesulfonamide;

[2-trifluoromethyl-5-(3,4-difluorophenyl)-4-oxazolyl]benzenesulfonamide;

4-[2-methyl-4-phenyl-5-oxazolyl]benzenesulfonamide; and

4-[5-(3-fluoro-4-methoxyphenyl-2-trifluoromethyl)-4-oxazolyl]benzenesulfonamide.

9. A method of treating a condition selected from inflammation or an inflammation-associated disorder in a subject, said method comprising administering to the subject having or susceptible to such indication or inflammation-associated disorder, a therapeutically-effective amount of a cyclooxygenase-2 inhibitor selected from N-2-cyclohexyloxy-4-nitrophenyl)methanesulfonamide, meloxicam, flosulide and compounds of Formula I

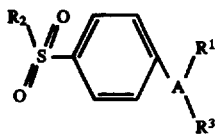
I wherein

A is a 5- or 6-member ring substituent selected from partially unsaturated or unsaturated heterocyclo and carbocyclic rings;

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl, and amino; and wherein $R^3$ is a radical selected from halo, alkyl, alkenyl, alkynyl, oxo, cyano, carboxyl, cyanoalkyl, heterocyclooxy, alkyloxy, alkylthio, alkylcarbonyl, cycloalkyl, aryl, haloalkyl, heterocyclo, cycloalkenyl, aralkyl, heterocycloalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof;

and a leukotriene $A_4$ hydrolase inhibitor selected from compounds of Formula II $$Ar^1—Q—Ar^2—Y—R—Z \qquad (II)$$

or a pharmaceutically-acceptable salt thereof, and a pharmaceutically-acceptable carrier, wherein $Ar^1$ is an aryl moiety selected from:
  (i) phenyl, mono-, di-, or tri-substituted phenyl with the substituents selected from Cl, Br, F, $CF_3$, lower alkyl, lower alkoxy, $NH_2$, $NO_2$ and OH;
  (ii) 2-, 4- or 5-thiazolyl,
  (iii) 2-, 3- or 4-pyridinyl,
  (iv) 2- or 3-thienyl, and
  (v) 2- or 3-furyl;

wherein $Ar^2$ is an aryl moiety selected from:

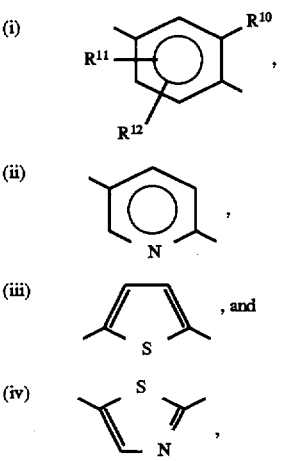

wherein

Q is selected from:
  (i) —O—,
  (ii) —$CH_2$—,
  (iii) —$OCH_2$—,
  (iv) —$CH_2O$—,
  (v) —NH—;
  (vi) —$NHCH_2$—,
  (vii) —$CH_2NH$—,
  (viii) —$CF_2$—,
  (ix) —CH=CH—, (x) —CH$_2$CH$_2$—, and
(xi) carbon-carbon single bond;
wherein
Y is selected from:
(i) —O—,
(ii) —S—,
(iii) —NH—,
(iv) —S(O)—, and
(v) —S(O$_2$)—;
wherein
R is selected from:
(i) linear or branched C$_2$–C$_6$ alkylenyl; and
(ii) —C(R$^{13}$)(R$^{14}$)—(CH$_2$)$_m$—;
wherein
Z is selected from:

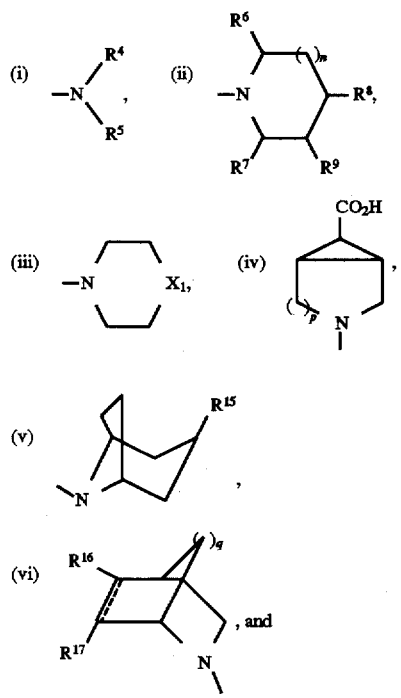

(viii) a monocyclic or bicyclic heteroaromatic moiety having at least one heteroatom, wherein the heteroatom is nitrogen, and wherein the monocyclic heteroaromatic moiety comprises a 5- or 6-membered ring and the bicyclic heteroaromatic moiety comprises a fused 9- or 10-membered ring;
wherein
R$^4$ and R$^5$ are independently selected from:
(i) H,
(ii) lower alkyl or allyl,
(iii) benzyl,
(iv) —(CH$_2$)$_a$COR$^{18}$,
(v)

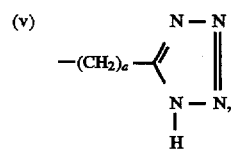

and
(vi) —(CH$_2$)$_a$—OH;
wherein

R$^6$ and R$^7$ are independently H or lower alkyl;
wherein
R$^8$ and R$^9$ are independently selected from (i) H
(ii) —OH, =O or —(CH$_2$)$_a$—OH,
(iii) —(CH$_2$)$_a$COR$^{18}$
(iv) —(CH$_2$)$_a$CONH(CH$_2$)$_b$CO$_2$R$^{19}$,
(v) —NHR$^{20}$, (vi) 
<br>N—N
<br>—⫽ ‖
<br>N—N
<br>|
<br>H (vii) 
<br>N—OH
<br>—⫽
<br>NH$_2$ , (viii) 
<br>NH
<br>—⫽
<br>NH$_2$, and (ix) 
<br>N—O
<br>—⫽   \
<br>HN—⫽
<br>     \\
<br>      O ;

wherein
R$^{10}$ is H, halogen, lower alkyl, lower alkoxy, nitro, or hydroxy, or R$^{10}$ taken together with R$^{13}$ is an alkylenyl group having one or two carbon atoms;
wherein
R$^{11}$ and R$^{12}$ are independently H, halogen, lower alkyl, lower alkoxy, NH$_2$, NO$_2$ or OH;
wherein
R$^{13}$ is H, or lower alkyl, or R$^{13}$ taken together with R$^{10}$ is an alkylenyl group having one or two carbon atoms;
wherein
R$^{14}$ is H or lower alkyl;
wherein
R$^{15}$ is selected from
(i) H,
(ii) —OH or =O,
(iii) —(CH$_2$)$_a$COR$^{18}$
(iv) —(CH$_2$)$_a$CONH(CH$_2$)$_b$CO$_2$R$^{19}$, and
(v) —NHR$^{20}$;
wherein
R$^{16}$ and R$^{17}$ are independently hydrogen, or —(CH$_2$)$_a$COR$^{18}$, provided that at least one of R$^{16}$ and R$^{17}$ is hydrogen;
wherein
R$^{18}$ is —OR$^{19}$, —NMR$^{19}$ or —NHNH$_2$;
wherein
R$^{19}$ is H, lower alkyl or benzyl;
wherein
R$^{20}$ is H, lower alkyl, benzyl, —COR$^{19}$ or —CONH$_2$;
wherein $X^1$ is

—S—, or —O—, wherein $R^{21}$ is H, lower alkyl, —$CONH_2$, —$CSNH_2$, —$COCH_3$ or —$SO_2CH_3$;

wherein a and b are independently integers of from 0 to 5;

wherein m is 1, 2 or 3;

wherein n is 0, 1, 2 or 3;

wherein p is 1 or 2; and wherein q is 1, 2 or 3;

provided however that where R is —$C(R^{13})(R^{14})$—$CH_2$)$_n$—, and $R^{13}$ taken together with $R^{10}$ forms an alkylenyl group having one or two carbon atoms, then —$Ar^2$—Y—R— is

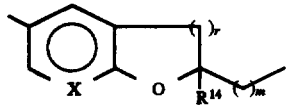

wherein

X is —CH— or —N—; and wherein r is 1 or 2; further provided that wherein Z is

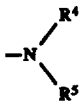

and either $R^4$ or $R^5$, or both $R^4$ and $R^5$ are —$(CH_2)_aCOR^{18}$, then a is not 0.

10. The method of claim 9 wherein said leukotriene $A_4$ hydrolase inhibitor and said cycloxygenase-2 inhibitor are administered in a sequential manner.

11. The method of claim 9 wherein said leukotriene $A_4$ hydrolase inhibitor and said cycloxygenase-2 inhibitor are administered in a substantially simultaneous manner.

12. The method of claim 9, wherein the leukotriene $A_4$ hydrolase inhibitor is selected from ethyl-1-[2-[4-(phenylmethyl)phenoxy]ethyl]-piperidine-carboxylate;

1-[2-[4-(phenylmethyl)phenoxy]ethyl]-2-methyl-4-tetrazolylpiperidine;

1-[2-[4-(4-(2-oxazolyl)phenoxy)phenoxy]ethyl] pyrrolidine;

3-[methyl[3-[4-(2-thienylmethyl)phenoxy]propyl]amino] propanoic acid;

methyl-3-[methyl[3-[4-(2-thienylmethyl)phenoxy] propyl]amino]propanoate;

3-[methyl[3-[4-(3-thienylmethyl)phenoxy]propyl]amino] propanoic acid;

methyl-3-[methyl[3-[4-(3-thienylmethyl)phenoxy] propyl]amino]propanoate;

3-[methyl[3-[4-(phenylmethyl)phenoxy]propyl]amino] propanoic acid;

3-[methyl[3-[4-(4-fluorophenoxy)phenoxy]propyl] amino]propanoic acid; and

3-[methyl[3-[4-(4-biphenyloxy)phenoxy]propyl]amino] propanoic acid.

13. The method of claim 9 wherein A is selected from oxazolyl, isoxazolyl, dihydrofuryl, imidazolyl, and pyrazolyl; wherein $R^1$ is selected from 5- and 6-membered heterocyclo, and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is amino; and wherein $R^3$ is a radical selected from oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclo, lower hydroxylalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

14. The method of claim 13 wherein A is selected from oxazolyl, isoxazolyl, imidazolyl, and pyrazolyl; wherein $R^1$ is phenyl optionally substituted at a substitutable position with one or more radicals selected from methyl, ethyl, isopropyl, butyl, tert-butyl, isobutyl, pentyl, hexyl, trifluoromethyl, cyano, carboxyl, methoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, nitro, methoxymethyl, methylsulfinyl, fluoro, chloro, bromo, methoxy, ethoxy, propoxy, n-butoxy, pentoxy, and methylthio; wherein $R^2$ is amino; and wherein $R^3$ is a radical selected from oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminoethyl, benzyloxy, and phenyloxy; or a pharmaceutically-acceptable salt thereof.

15. The method of claim 14, wherein the leukotriene $A_4$ hydrolase inhibitor is selected from compounds, their prodrugs and their pharmaceutically-acceptable salts, of the group consisting of 4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(3-fluoro-4-methoxyphenyl)-3-(difluoromethyl)-1H-pyrazol-1-yl]benzenesulfonamide;

3-[1-[4-(methylsulfonyl)phenyl]-4-trifluoromethyl-1H-imidazol-2-yl]pyridine;

2-methyl-5-[1-[4-(methylsulfonyl)phenyl]-4-trifluoromethyl-1H-imidazol-2-yl]pyridine;

4-[2-(5-methylpyridin-3-yl)-4-(trifluoromethyl)-1H-imidazol-1-yl]benzenesulfonamide;

4-[5-methyl-3-phenylisoxazol-4-yl]benzenesulfonamide;

4-[5-hydroxyethyl-3-phenylisoxazol-4-yl]benzenesulfonamide;

[2-trifluoromethyl-5-(3,4-difluorophenyl)-4-oxazolyl]benzenesulfonamide;

4-[2-methyl-4-phenyl-5-oxazolyl]benzenesulfonamide; and

4-[5-(3-fluoro-4-methoxyphenyl-2-trifluoromethyl)-4-oxazolyl]benzenesulfonamide.

16. The method of claim 9 wherein the condition is inflammation.

17. The method of claim 9 wherein the condition is an inflammation-associated disorder.

18. The method of claim 17 wherein the inflammation-associated disorder is arthritis.

19. The method of claim 9 wherein the subject is susceptible to inflammation.

20. The method of claim 9 wherein the subject is susceptible to an inflammation-associated disorder.

21. The method of claim 20 wherein the subject is susceptible to arthritis.

* * * * *